United States Patent [19]

Trummlitz et al.

[11] 4,233,299
[45] Nov. 11, 1980

[54] 4-HYDROXY-2H-1,2-BENZOTHIAZINE-3-CARBOXAMIDE-1,1-DIOXIDES AND SALTS THEREOF

[75] Inventors: Günter Trummlitz; Wolfhard Engel; Ernst Seeger; Günther Engelhardt, all of Biberach an der Riss, Fed. Rep. of Germany

[73] Assignee: Boehringer Ingelheim GmbH, Fed. Rep. of Germany

[21] Appl. No.: 966,963

[22] Filed: Dec. 6, 1978

[30] Foreign Application Priority Data

Dec. 16, 1977 [DE] Fed. Rep. of Germany ....... 2756113

[51] Int. Cl.³ .................... C07D 417/12; A61K 31/38
[52] U.S. Cl. ........................................ 424/246; 544/49
[58] Field of Search .......................... 424/246; 544/49

[56] References Cited

U.S. PATENT DOCUMENTS

| | | | |
|---|---|---|---|
| 3,591,584 | 7/1971 | Lombardino | 544/49 |
| 3,853,862 | 12/1974 | Lombardino | 544/49 |
| 3,892,740 | 7/1975 | Lombardino | 544/49 |
| 3,925,371 | 12/1975 | Rasmussen | 544/49 |
| 4,100,347 | 7/1978 | Hammen | 544/49 |
| 4,116,964 | 9/1978 | Zinnes et al. | 544/49 |

Primary Examiner—John M. Ford
Attorney, Agent, or Firm—Hammond & Littell, Weissenberger & Muserlian

[57] ABSTRACT

Compounds of the formula

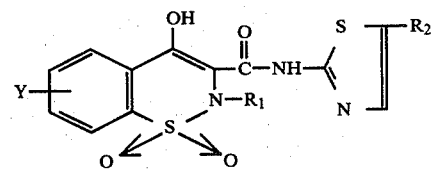

wherein
$R_1$ is hydrogen, methyl or ethyl;
$R_2$ is methyl, ethyl or n-propyl; and
Y is hydrogen, methyl, methoxy, fluorine or chlorine;

and non-toxic, pharmacologically acceptable salts thereof formed with an inorganic or organic base. The compounds as well as their salts are useful as antiphlogistics.

5 Claims, No Drawings

4-HYDROXY-2H-1,2-BENZOTHIAZINE-3-CARBOXAMIDE-1,1-DIOXIDES AND SALTS THEREOF

This invention relates to novel 4-hydroxy-2H-1,2-benzothiazine-3-carboxamide-1,1-dioxides and salts thereof, as well as to methods of preparing these compounds, pharmaceutical compositions containing them as active ingredients, and methods of using them as antiphlogistics.

THE PRIOR ART

German Offenlegungsschrift No. 1,943,265 discloses 3,4-dihydro-2H-1,2-benzothiazine-1,1-dioxides which are structurally related to the compounds of the present invention.

THE INVENTION

More particularly, the present invention relates to a novel class of compounds represented by the formula

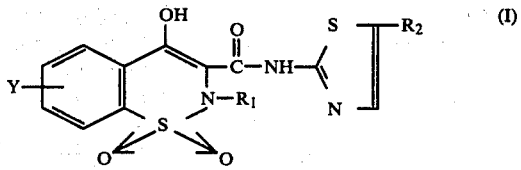

wherein
- $R_1$ is hydrogen, methyl or ethyl;
- $R_2$ is methyl, ethyl or n-propyl; and
- Y is hydrogen, methyl, methoxy, fluorine or chlorine;

and non-toxic, pharmacologically acceptable salts thereof formed with an inorganic or organic base.

The compounds embraced by formula I may be prepared by the following methods:

Method A

By reacting a 4-hydroxy-2H-1,2-benzothiazine-1,1-dioxide-3-carboxylic acid derivative of the formula

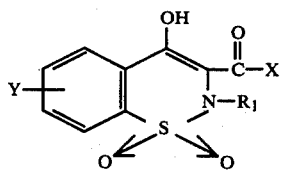

wherein
- X is a nucleophilic exchangeable group, especially alkoxy of 1 to 8 carbon atoms, phenylalkoxy of 7 to 10 carbon atoms, phenoxy, halogen, amino, alkylamino of 1 to 8 carbon atoms, cycloalkylamino of 3 to 10 carbon atoms, phenylalkylamino of 7 to 10 carbon atoms or anilino; and
- $R_1$ and Y have the same meanings as in formula I, with an aromatic amine of the formula

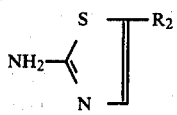

wherein $R_2$ has the same meanings as in formula I.

The reaction is advantageously carried out in an inert organic solvent, for example in an aromatic hydrocarbon such as benzene, toluene, xylene, chlorobenzene, o-dichlorobenzene or tetrahydronaphthaline; or in dimethylformamide, dimethylacetamide or dimethylsulfoxide; or in hexamethylphosphoric acid triamide; or in an ether such as dimethoxyethane, diethyleneglycol dimethyl ether or diphenyl ether; or also without a solvent in an excess of the amine of the formula III. The reaction is carried out at temperatures between 20° and 180° C. Preferably, the reaction is carried out in toluene or xylene at the boiling point, and the resulting alcohol is removed during the reaction by azeotropic distillation or by refluxing, for example using a Soxhlet extractor equipped by a molecular sieve, if in formula II X represents an alkoxy group. The product is obtained from the reaction mixture in crystalline form, or it is precipitated from a water-miscible solvent by adding water.

If X in formula II represents the amino group or, as mentioned above, a substituted amino group, then during the reaction preferably a catalytic amount of p-toluenesulfonic acid is added, and the aromatic amine of formula III is provided in excess. In this case the product also often crystallizes directly from the reaction mixture, but in any case it can be obtained by evaporating the solvent; it can also be precipitated from a water-miscible solvent by addition of water.

Method B

Compounds of the formula I wherein $R_1$ represents a methyl or ethyl group and $R_2$ and Y have the meanings defined above can also be obtained by reaction of the 4-hydroxy-2H-1,2-benzothiazine-3-carboxamide-1,1-dioxide of the formula

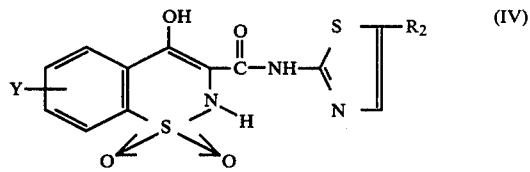

wherein $R_2$ and Y have the meanings previously defined, with an alkyl halide of the formula $$R_{11}-Hal \qquad (V)$$

wherein
- Hal represents a halogen atom, and
- $R_{11}$ represents a methyl or ethyl group, in the presence of a base.

As bases can be used alkali metal or alkaline earth metal hydroxides, for example sodium, potassium or barium hydroxide; or alkali metal or alkaline earth metal carbonates such as sodium or potassium carbonate; as well as alkali metal or alkaline earth metal alcoholates, for example sodium methylate, potassium ethylate, potassium tert.butylate; or tertiary amines, for example triethylamine, if the reaction is carried out in an aqueous medium, in an alcoholic medium such as in methanol, ethanol, n-propanol, isopropanol or in mixtures of the indicated solvents.

The alkyl halide, preferably an alkyl bromide or an alkyl iodide, is added advantageously in alcoholic solution directly to the other reaction partners present in the reaction mixture, where in the case of methyl bromide the reaction is carried out in a closed vessel. As further solvents may be considered: dimethylformamide, dimethylacetamide, dimethylsulfoxide or hexamethylphosphoric acid triamide.

If alkali metal carbonates or alkaline earth metal carbonates are used as bases, aliphatic ketones, such as acetone, can be used as solvents.

If the reaction is carried out in an aprotic organic solvent, such as benzene, or in another aromatic hydrocarbon, in tetrahydrofuran or in another acyclic or cyclic ether, alkali metal hydrides or alkaline earth metal hydrides for example sodium hydride, can be used as bases. In that case the alkyl halide is not added until after the alkali metal hydride or the alkaline earth metal hydride has completely reacted with the starting compound of the formula IV. The reaction temperature is 0° to 80° C.

In some cases it is advisable, before carrying out the two aforementioned methods, to protect the 4-hydroxy group in the compounds of the formula II or IV by a protective group, where this protective group is removed again after the reaction is completed. Thus, for example, an etherification of the 4-hydroxy groups is of advantage; these hydroxyl groups are converted according to known methods into the corresponding alkoxy or phenylalkoxy groups, for example into alkoxy groups of 1 to 8 carbon atoms or into phenylalkoxy groups of 7 to 10 carbon atoms. After the reaction these groups are removed, for example by heating in a mineral acid, such as hydrobromic acid, to temperatures up to 100° C., or by addition of a borontrihalide, such as borontribromide or borontrichloride, in an inert solvent such as a chlorinated hydrocarbon at temperatures between −80° to +80° C.

The compounds embraced by formula I form salts with inorganic or organic bases. Examples of non-toxic, pharmacologically acceptable salts are those formed with alkali metal alcoholates, alkali metal hydroxides, alkaline earth metal hydroxides, trialkylammonium hydroxides, alkylamines, or preferably amino-polyalcohols, especially N-methyl-D-glucamine. The N-methyl-D-glucamine salts are of particular importance because they are eminently suitable for the preparation of injectable solutions.

The starting compounds of the formula II, wherein X represents an alkoxy, phenylalkoxy or phenoxy radical, are generally known and can be prepared, for example, according to the method described in German Offenlegungsschrift No. 1,943,265 (see also U.S. Pat. No. 3,591,584); thus, to prepare these starting compounds, one starts, for example, from the known esters of N-(alkoxycarbonyl-methyl)-1,2-benzisothiazol-3-one-1,1-dioxide (Chem. Berichte 30, 1267 [1897]), and an alkali metal alcoholate is added to them, for example sodium ethanolate, in an organic polar solvent such as dimethylsulfoxide or dimethylformamide.

Thereby a rearrangement reaction begins, and after acidification the corresponding ester of the formula II wherein $R_1$ represents hydrogen is obtained. If it is desired to add to this ester in 2-position the other groups which are included in the definition $R_1$ above, this is most advantageously accomplished by means of an alkylhalide, preferably by means of an alkyl iodide; the alkylation is carried out in the presence of a base.

The starting compounds of the formula II wherein X represents an amino group or a substituted amino group are known from the literature. They can be prepared, for example, according to the method described in German Offenlegungsschrfit No. 1,943,265 (see also U.S. Pat. No. 3,591,584) from a 4-hydroxy-2H-1,2-benzothiazine-3-carboxylate-1,1-dioxide of the formula II by reaction with an amine of the formula $NH_2-R_4$, wherein $R_4$ represents a hydrogen atom, an alkyl group of 1 to 8 carbon atoms, a cycloalkyl group of 3 to 10 carbon atoms, a phenylalkyl group of 7 to 10 carbon atoms or the phenyl group, in an inert solvent, such as dimethylsulfoxide or tert. butanol, at temperatures between 20° and 200° C.

The starting compounds of the formula II wherein X represents halogen can be obtained, for example, by reaction of the corresponding 4-hydroxy-2H-1,2-benzothiazine-3-carboxylic acid-1,1-dioxide with a thionylhalide in a solvent such as benzene or dimethylformamide at temperatures up to the reflux temperature of the reaction mixture.

The compounds of the formula III are also known from the literature (see H. Erlenmeyer, Z. Herzfeld and B. Prijs, Helv. chim. Acta 38, 1291 [1955]; or K.D. Kulkarni and M. V. Shirsat, J. Sci. and Ind. Research (India), 18B, 411 [1959]; or C. A. 54, 14230 d [1960]).

The starting compounds of the formula IV may be prepared, for example, from a 4-hydroxy-2H-1,2-benzothiazine-3-carboxylate-1,1-dioxide of the formula II wherein $R_1$ represents hydrogen by reaction with an aromatic amine of the formula III in a suitable inert organic solvent at temperatures between 20° to 180° C.

The following examples illustrate the present invention and will enable others skilled in the art to understand it more completely. It should be understood, however, that the invention is not limited solely to the particular examples given below.

EXAMPLE 1

4-Hydroxy-2-methyl-N-(5-methyl-2-thiazolyl)-2H-1,2-benzothiazine-3-carboxamide-1,1-dioxide A mixture of 26.9 gm (0.1 mol) of the 1,1-dioxide of methyl 4-hydroxy-2-methyl-2H-1,2-benzothiazine-3-carboxylate and 12.5 gm (0.11 mol) of 2-amino-5-methyl-thiazole was refluxed in 4 liters of xylene for 24 hours in a nitrogen atmosphere. The methanol formed by the reaction was removed by means of a 4-Å-molecular sieve mounted in a Soxhlet-extractor. The hot reaction solution was filtered. Upon cooling and standing overnight, the crude product separated out of the filtrate in the form of crystals (32.0 gm = 91% of theory). After recrystallization from ethylene chloride 26.0 gm (74% of theory) of 4-hydroxy-2-methyl-N-(5-methyl-2-thiazolyl)-2H-1,2-benzothiazine-3-carboxamide-1,1-dioxide were obtained.

M.p.: 254° C. (decomp.).

1H-NMR ([$D_6$]-DMSO): $\delta = 8.2-7.8$ (m, 4, 5-H to 8-H); 7.36 (d, 1, J = 0.75 Hz, 4'-H); 2.90 (s, 3, N—$CH_3$); 3.36 (d, 3, J = 0.75 Hz, 5' = $CH_3$) and 2 exchangeable protones. $C_{14}H_{13}N_3O_4S_2$ (351.40)

Calc: C-47.85%; H-3.73%; N-11.96%; S-18.21%.
Found: C-47.65%; H-3.72%; N-11.72%; S-18.40%.

EXAMPLE 2

Sodium Salt of 4-Hydroxy-2-methyl-N-(5-methyl-2-thiazolyl)-2H-1,2-benzothiazine-3-carboxamide-1,1-dioxide 7.0 gm (20 millimols) of 4-hydroxy-2-methyl-N-(5-methyl-2-thiazolyl)-2H-1,2-benzothiazine-3-carboxamide-1,1-dioxide were added to a solution of 1.1 gm (20 millimols) of sodium methylate in 200 ml of methanol.

The mixture was heated, and the resulting yellow solution was filtered and evaporated to dryness in vacuo. Acetone and ether were added to the residue, the mixture was filtered yielding 7.25 gm (97.5% of theory) of the sodium salt of 4-hydroxy-2-methyl-N-(5-methyl-2-thiazolyl)-2H-1,2-benzothiazine-3-carboxamide-1,1-dioxide.

M.p.: 214° C. (decomp.).

EXAMPLE 3

N-Methyl-D-glucamine salt of 4-Hydroxy-2-methyl-N-(5-methyl-2-thiazolyl)-2H-1,2-benzothiazine-3-carboxamide-1,1-dioxide 6.0 gm (17.1 millimols) of 4-hydroxy-2-methyl-N-(5-methyl-2-thiazolyl)-2H-1,2-benzothiazine-3-carboxamide-1,1-dioxide and 3.33 gm (17.1 millimols) of N-methyl-D-glycamine were dissolved in 1 liter of distilled water. After heating it to 60° C., the solution was filtered. The filtrate was evaporated in vacuo to 60 ml. The crystalline 4-hydroxy-2-methyl-N-(5-methyl-2-thiazolyl)-2H-1,2-benzothiazine-3-carboxamide-1,1-dioxide N-methyl-D-glycamine salt, thus obtained, was filtered off and dried in vacuo at 80° C. over phosphorus pentoxide. Yield: 5.2 gm (56% of theory).

M.p.: 110° C.

$C_{21}H_{30}N_4O_9S_2$ (546.63)

Calc.: C-46.14%; H-5.53%; N-10.25%; S-11.73%.
Found: C-45.95%; H-5.76; N-10.24; S-11.98%.

EXAMPLE 4

4-Hydroxy-N-(5-methyl-2-thiazolyl)-2H-1,2-benzothiazine-3-carboxamide-1,1-dioxide Prepared from methyl 4-hydroxy-2H-1,2-benzothiazine-3-carboxylate-1,1-dioxide and 2-amino-5-methylthiazole analogous to Example 1. The crude product (65% of theory) was purified by column chromatography (Merck-silica gel 60, particle size: 0.2–0.5 mm), using chloroform/ethanol (97:3) as eluant. 4-Hydroxy-N-(5-methyl-2-thiazolyl)-2H-1,2-benzothiazine-3-carboxamide-1,1-dioxide was obtained with a yield of 31% of theory.

M.p.: 233° C. (decomp.) from ethylene chloride.

$C_{13}H_{11}N_3O_4S_2$ (337.38)

Calc.: C-46.29%; H-3.29%; N-12.45%; S-19.01%.
Found: C-46.20%; H-3.34%; N-12.52% S-19.12%.

EXAMPLE 5

2-Ethyl-4-hydroxy-N-(5-methyl-2-thiazolyl)-2H-1,2-benzothiazine-3-carboxamide-1,1-dioxide Prepared from methyl 2-ethyl-4-hydroxy-2H-1,2-benzothiazine-3-carboxylate-1,1-dioxide and 2-amino-5-methylthiazole analogous to Example 1 with a yield of 82% of theory.

M.p.: 247° C. (decomp.) from xylene.

$C_{15}H_{15}N_3O_4S_2$ (365.43)

Calc.: C-49.30%; H-4.14%; N-11.50%; S-17.55%.
Found: C-49.25%; H-4.07%; N-11.40%; S-17.72%.

EXAMPLE 6

N-(5-Ethyl-2-thiazolyl)-4-hydroxy-2-methyl-2H-1,2-benzothiazine-3-carboxamide-1,1-dioxide Prepared from methyl 4-hydroxy-2-methyl-2H-1,2-benzothiazine-3-carboxylate-1,1-dioxide and 5-ethyl-2-amino-thiazole analogous to Example 1 with a yield of 67% of theory.

M.p.: 260° C. (decomp.) from xylene.

$C_{15}H_{15}N_3O_4S_2$ (365.43)

Calc.: C-49.30%; H-4.14%; N-11.50%; S-17.55%.
Found: C-49.20%; H-4.19%; N-11.30%, S-17.63%.

EXAMPLE 7

4-Hydroxy-2-methyl-N-(5-N-(5-n-propyl-2-thiazolyl)-2H-1,2-benzothiazine-3-carboxamide-1,1-dioxide Prepared from methyl 4-hydroxy-2-methyl-2H-1,2-benzothiazine-3-carboxylate-1,1-dioxide and 2-amino-5n-propyl-thiazole in toluene analogous to Example 1 with a yield of 48% of theory.

M.p.: 210° C. (decomp.) from dioxane/petroleum ether.

$C_{16}H_{17}N_3O_4S_2$ (379.46)

Calc.: C-50.64%; H-4.52%; N-11.07%; S-16.90%.
Found: C-50.90%; H-4.64%; N-10.97%; S-17.00%.

EXAMPLE 8

2,6-Dimethyl-4-hydroxy-N-(5-methyl-2-thiazolyl)-2H-1,2-benzothiazine-3-carboxamide-1,1-dioxide 4.0 gm (14 millimols) of methyl 4-hydroxy-2,6-dimethyl-2H-1,2-benzothiazine-3-carboxylate-1,1-dioxide and 2.0 gm (17 millimols) of 2-amino-5-methylthiazole were refluxed in 200 ml of anhydrous xylene for 24 hours. After cooling, the crystals which had separated out were filtered off. After recrystallization from ethylene chloride 3.6 gm (70% of theory) of 2,6-dimethyl-4-hydroxy-N-(5-methyl-2-thiazolyl)-2H-1,2-benzothiazine-3carboxamide-1,1-dioxide were obtained.

M.p.: 257° C. (decomp.).

1H-NMR (CDCl$_3$+TFA): δ=7.98 (br s, 1, 5-H), 7,92 (d, 1, J=4Hz, 8-H), 7.7 (br d, 1, J=4HZ, 7-H), 7.47 (d, 1, J=1Hz, 4'-H), 2.96 (s, 3, N—CH$_3$) and 2.6 (br s, 6, 6—CH$_3$ and 5'—CH$_3$).

$C_{15}H_{15}N_3O_4S_2$ (365.45)

Calc.: C-49.30%; H-4.14%; N-11.50%; S-17.55%
Found: C-49.40%; H-4.24%; N-11.45% S-17.35%.

If instead of xylene o-dichloro-benzene, tetrahydronaphthaline or diethyleneglycol dimethylether was used as the solvent, the same compound was obtained with yields of 70, 60 and 75%, respectively.

The starting compound was prepared as follows: 45 gm (0.23 mol) of 5-methyl-benzisothiazole-3(2H)-one-1,1-dioxide were added to a solution of 9.16 gm (0.23 mol) of sodium hydroxide in 500 ml of water, and the mixture was heated to the boiling point. The resulting solution was filtered and evaporated in vacuo, toluene was several times added to the residue, and the toluene was distilled off each time. Then, 200 ml of dimethylsulfoxide and 34.72 gm (0.32 mol) of methyl chloroacetate were added to the residue. The reaction mixture was heated at 120° C. for 3 hours, and after cooling it was stirred into a solution of 42 gm of sodium acetate in 300 ml of water. The precipitate was filtered off, washed with water, treated again with 200 ml of water which was removed by suction, and then the precipitate was dried. 48.8 gm (79% of theory) of methyl 5-methyl-3-oxo-benzisothiazolo-2(3H)-acetate-1,1-dioxide were obtained.

M.p.: 115° C.

38 gm (0.14 mol) of methyl 5-methyl-3-oxo-benzisothiazolo-2(3H)-acetate-1,1-dioxide were admixed with 23.9 gm (0.44 mol) of sodium methylate, and first 250 ml of anhydrous toluene and then 42 ml of anhydrous tert. butanol were added while vigorously stirring the mixture. Subsequently, the yellow reaction mixture was heated for 1 hour at 65° C. After cooling, the reaction mixture was poured into ice water, and ether was added. The aqueous phase was twice extracted with ether and carefully acidified with concentrated aqueous hydrochloric acid. After extracting with ether again, the ether phase was washed with water, dried and evaporated. The residue was recrystallized from ethyl acetate, yielding 27.6 gm (73% of theory) of methyl 4-hydroxy-6-methyl-2H-1,2-benzothiazine-3-caboxylate-1,1-dioxide.

M.p.: 169° C.

25 gm (0.092 mol) of methyl 4-hydroxy-6-methyl-2H-1,2-benzothiazine-3-carboxylate-1,1-dioxide and 36.9 gm (0.26 mol) of methyl iodide were suspended in 185 ml of tetrahydrofuran. A solution of 5.2 gm (0.092 mol) of potassium hydroxide in 100 ml of water was added to the suspension. After 24 hours another 20 gm of methyl iodide were added, and after 24 hours of stirring methyl 2,6-dimethyl-4-hydroxy-2H-1,2-benzothiazine-3-carboxylate-1,1-dioxide was filtered off, washed and dried. Yield: 9.9 gm (38% of theory).

M.p.: 186° C.

EXAMPLE 9

2,7-Dimethyl-4-hydroxy-N-(5-methyl-2-thiazolyl)-2H-1,2-benzothiazine-3-carboxamide-1,1-dioxide 2.83 gm (0.01 mol) of methyl 2,7-dimethyl-4-hydroxy-2H-1,2-benzothiazine-3-carboxylate-1,1-dioxide and 1.25 gm (0.011 mol) of 2-amino-5-methyl-thiazole were reacted in xylene analogous to Example 8, and 3.1 gm (84% of theory) of 2,7-dimethyl-4-hydroxy-N-(5-methyl-2-thiazolyl)-2H-1,2-benzothiazine-3-carboxamide-1,1-dioxide were obtained M.p.: 228° C. (from xylene).

When the reaction was performed in toluene, the same product was obtained with a yield of 70%.

$C_{15}H_{15}N_3O_4S_2$ (365.45)

Calc.: C-49.30%; H-4.14%; N-11.50%; S-17.55%. Found: C-49.25%; H-4.08%; N-11.41% S-17.62%.

The starting compound was prepared by conversion of 6-methyl-benzisothiazole-3(2H)-one-1,1-dioxide, analogous to 5-methyl-benzisothiazole-3(2H)-one-1,1-dioxide (see Example 8), with sodium hydroxide and methyl chloroacetate into methyl 6-methyl-3-oxo-benzisothiazolo-2(3H)-acetate-1,1-dioxide (M.p.: 139° C. from methanol). By subsequent rearrangement with sodium methylate in toluene/tert. butanol, methyl 4-hydroxy-7-methyl-2H-1,2-benzothiazine-3-carboxylate-1,1-dioxide was obtained, which, by reaction with methyl iodide, produced methyl 2,7-dimethyl-4-hydroxy-2H-1,2-benzothiazine-3-carboxylate-1,1-dioxide.

M.p.: 183° C.

EXAMPLE 10

4-Hydroxy-6-methoxy-2-methyl-N-(5-methyl-2-thiazolyl)-2H-1,2-benzothiazine-3-carboxamide-1,1-dioxide 5.2 gm (0.017 mol) of methyl 4-hydroxy-6-methoxy-2-methyl-2H-1,2-benzothiazine-3-caboxylate-1,1-dioxide and 2.2 gm (0.019 mol) of 2-amino-5-methyl-thiazole were refluxed in 200 ml of xylene for 24 hours. After cooling, the precipitated crystals were filtered off and recrystallized from tetrahydrofuran. 5.8 gm (89% of theory) of 4-hydroxy-6-methoxy-2-methyl-N-(5-methyl-2-thiazolyl)-2H-1,2-benzothiazine-3-caboxamide-1,1-dioxide were obtained.

M.p.: 260° C.

1H-NMR (CDCl$_3$)+TFA): δ=7.95 (d, 1, J=4 Hz, 8-H), 7.62 (d, 1, J=1, 5 Hz, 5-H), 7.45 (d, 1, J=1 Hz, 4'-H), 7.35 (dd, 1, J=4 Hz and J'=1, 5 Hz, 6-H), 4.00 (s, 3, OCH$_3$), 2.95 (s, 3, N—CH$_3$) and 2.55 (d, 3, J=1 Hz, 5'—CH$_3$).

$C_{15}H_{15}N_3O_5S_2$ (381.45)

Calc.: C-47.23%; H-3.96%; N-11.02%, S-16.81%. Found: C-47.50%; H-4.10%; N-10.87%; S-16.58%.

The starting compound was prepared by conversion of 5-methoxy-benzisothiazole-3(2H)-one-1,1-dioxide, analogous to 5-methyl-benzisothiazole-3(2H)-one-1,1-dioxide (see Example 8), with sodium hydroxide and methyl chloroacetate into methyl 5-methoxy-3-oxo-benzisothiazolo-2(3H)-acetate-1,1-dioxide. Methyl 4-hydroxy-6-methoxy-2H-1,2-benzothiazine-3-carboxylate-1,1-dioxide (m.p. 183° C., from ethyl acetate/cyclohexane) was obtained by subsequent rearrangement with sodium methylate in toluene/tert. butanol, and methyl 4-hydroxy-6-methoxy-2-methyl-2H-1,2-benzothiazine-3-carboxylate-1,1-dioxide was obtained by subsequent methylation.

M.p.: 164° C.

EXAMPLE 11

6-Chloro-4-hydroxy-2-methyl-N-(5-methyl-2-thiazolyl)-2H-1,2-benzothiazine-3-carboxamide-1,1-dioxide 5.0 gm (16.5 millimols) of methyl 6-chloro-4-hydroxy-2-methyl-2H-1,2-benzothiazine-3-carboxylate-1,1-dioxide and 2.1 gm (18.5 millimols) of 2-amino-5-methyl-thiazole were refluxed in 300 ml of anhydrous xylene for 24 hours in a Soxhlet-apparatus equipped with a 4-Å-molecular sieve. After cooling, the crude product which had crystallized out was filtered off and recrystallized from dioxane. 4.9 gm (77% of theory) of 6-chloro-4-hydroxy-2-methyl-N-(5-methyl-2-thiazolyl)-2H-1,2-benzothiazine-3-carboxamide-1,1-dioxide were obtained.

M.p.: 285° C. (decomp.).

1H-NMR ([D$_6$]-DMSO): δ=8.05 and 7.9 (m, 3, 5-H, 7-H and 8-H); 7.36 (d, 1, J=1 Hz, 4'-H); 2.95(s, 3, N—CH$_3$); 2.35 (d, 3, J=1 Hz, 5'=CH$_3$) and 2 exchangeable protons.

$C_{14}H_{12}N_3O_4S_2$ (385.86)

Calc.: C-43.58%; N-3.13%; Cl-9.19%; N-10.89%; S-16.62%. Found: C-43.42%; H-3.21%; Cl-9.28%; N-10.68%; S-16.60%.

The starting compound was prepared as follows: 43.6 gm (0.18 mol) of the sodium salt of 5-chloro-benzisothiazole-3(2H)-one-1,1-dioxide (prepared from 5-chloro-benzisothiazole-3(2H)-one-1,1-dioxide and sodium hydroxide) and 35 ml (0.21 mol) of methyl chloroacetate were heated in 100 ml of dimethylsulfoxide at 120° C. for 3 hours. After cooling, 80 ml of dimethylsulfoxide were removed from the reaction mixture by vacuum distillation. The residue was stirred into 700 ml of water containing 100 gm of sodium acetate. The precipitated methyl 5-chloro-3-oxo-benzisothiazole-2(3H)-acetate-1,1-dioxide was suction-filtered off, washed and dried.

Yield: 31.9 gm (60% of theory).

M.p.: 118° C.

24.5 gm (84.5 millimols) of this compound were heated with 13.5 gm (253 millimols) of sodium methylate in 190 ml of anhydrous toluene (with addition of 17 ml of dry tert. butanol) at 80° C. for 45 minutes. The cool reaction mixture was stirred into ice water and extracted with ether. The aqueous phase was acidified with hydrochloric acid. The white precipitate obtained thereby was filtered off, washed three times with water and dried.

Yield: 14.6 gm (60% of theory) of methyl 6-chloro-4-hydroxy-2H-1,2-benzothiazine-3-carboxylate-1,1-dioxide.

M.p.: 221° C. (decomp.).

14.5 gm (50 millimols) of methyl 6-chloro-4-hydroxy-2H-1,2-benzothiazine-3-carboxylate-1,1-dioxide were reacted with 21.3 gm (150 millimols) of methyl iodide and 50 ml of 1N sodium hydroxide in 165 ml of methanol, yielding 12.35 gm (81% of theory) of methyl 6-chloro-4-hydroxy-2-methyl-2H-1, 2-benzothiazine-3-carboxylate-1,1-dioxide.

M.p.: 201° C.

EXAMPLE 12

7-Fluoro-4-hydroxy-2-methyl-N-(5-methyl-2-thiazolyl)-2H-1,2-benzothiazine-3-carboxamide-1,1-dioxide 0.29 gm (1 millimol) of methyl 7-fluoro-4-hydroxy-2-methyl-2H-1,2-benzothiazine-3-carboxylate-1,1-dioxide and 0.125 gm (1.1 millimols) of 2-amino-5-methyl-thiazole were refluxed in 50 ml of xylene for 24 hours. The reaction mixture was evaporated to dryness in vacuo, and the residue was recrystallized from xylene/cyclohexane. 0.21 gm (57% of theory) of 7-fluoro-4-hydroxy-2-methyl-N-(5-methyl-2-thiazolyl)-2H-1,2-benzothiazine-3-carboxamide-1,1-dioxide were obtained.

M.p.: 233° C.

When benzene was used as the solvent the same yield was obtained after heating for 30 hours.

$C_{14}H_{12}FN_3O_4S_2$ (369.40)

Calc.: C-45.52%; H-3.27%; N-11.38%; S-17.36%.
Found: C-45.40%; H-3.18%; N-11.42%; S-17.18%.

The starting compound was prepared as follows:

6-fluoro-benzisothiazolo-3(2H)-one-1,1-dioxide was reacted, analogous to 5-chloro-benzisothiazole-3(2H)-one-1,1-dioxide (see Example 11), with sodium hydroxide and methyl chloroacetate to form methyl 6-fluoro-3-oxo-benzisothiazole-2(3H)-acetate 1,1-dioxide. (M.p.: 86° C. from isopropanol/petroleum/ether). Methyl 7-fluoro-4-hydroxy-2H-1,2-benzothiazine-3-carboxylate-1,1-dioxide was obtained by subsequent rearrangement with sodium methylate (m.p. 206° C.) and, by reaction with methyl iodide, methyl 7-fluoro-4-hydroxy-2-methyl-2H-1,2-benzothiazine-3-carboxylate-1,1-dioxide (m.p.: 191° C. from ethylene chloride) was obtained.

EXAMPLE 13

4-Hydroxy-2-methyl-N-(5-methyl-2-thiazolyl)-2H-1,2-benzothiazine-3-carboxamide-1,1-dioxide Prepared from ethyl 4-hydroxy-2-methyl-2H-1,2-benzothiazine-3-carboxylate-1,1-dioxide and 2-amino-5-methylthiazole analogous to Example 1, but using o-dichlorobenzene as the solvent with a yield of 76% of theory.

M.p.: 254° C. (decomp.) from ethylene chloride,
$C_{14}H_{13}N_3O_4S_2$ (351.40)

Calc.: C-47.85%; H-3.73%; N-11.96%; S-18.21%.
Found: C-47.91% H-3.78%; N-11.80%; S-18.42%.

EXAMPLE 14

4-Hydroxy-2-methyl-N-(5-methyl-2-thiazolyl)-2H-1,2-benzothiazine-3-carboxamide-1,1-dioxide 1.23 gm (4.5 millimols) of 4-hydroxy-2-methyl-2H-1,2-benzothiazine-3-carboxylic acid chloride-1,1-dioxide were dissolved in 10 ml of dimethylformamide and 1.0 gm (9 millimols) of 2-amino-5-methyl-thiazole was added in portions. The reaction mixture was stirred at room temperature for 24 hours, and then 40 ml of water were added. The mixture was stirred at room temperature for 20 minutes, and the precipitate which had formed was filtered off, washed and dried. After recrystallization from ethylene chloride 0.4 gm (25% of theory) of 4-hydroxy-2-methyl-N-(5-methyl-2-thiazolyl)-2H-1,2-benzothiazine-3-carboxamide-1,1-dioxide were obtained.

M.p.: 254° C. (decomp.).
$C_{14}H_{13}N_3O_4S_2$ (351.40)

Calc.: C-47.85%; H-3.73%; N-11.96%; S-18.21%.
Found: C-47.75%; H-3.88%; N-11.69%; S-17.98%.

EXAMPLE 15

4-Hydroxy-2-methyl-N-(5-methyl-2-thiazolyl)-2H-1,2-benzothiazine-3-carboxamide-1,1-dioxide 1.0 gm (3 millimols) of 4-hydroxy-2-methyl-N-phenyl-2H-1,2-benzothiazine-3-carboxamide-1,1-dioxide were refluxed with 1.15 gm (10 millimols) of 2-amino-5-methyl-thiazole and 0.1 gm of p-toluenesulfonic acid in 250 ml of xylene for 72 hours. After cooling, the reaction mixture was washed with 2N hydrochloric acid and with water, dried and evaporated in vacuo. The residue was purified column-chromatographically (Merck-silica gel 60; particle size: 0.2–0.5 mm; eluant: chloroform/ethanol, 95:5), yielding 0.25 gm (24% of theory) of 4-hydroxy-2-methyl-N-(5-methy-2-thiazolyl)-2H-1,2-benzothiazine-3-caboxamide-1,1-dioxide.

M.p.: 254° C. (decomp.) from ethylene chloride.
$C_{14}H_{13}N_3O_4S_2$ (351.40)

Calc.: C-47.85%; H-3.73%; N-11.96%; S-18.21%.
Found: C-47.70%; H-3.78%; N-11.86%; S-18.01%.

EXAMPLE 16

4-Hydroxy-2-methyl-N-(5-methyl-2-thiazolyl)-2H-1,2-benzothiazine-3-carboxamide-1,1-dioxide Prepared from 4-hydroxy-2-methyl-2H-1,2-benzothiazine-3-carboxamide-1,1-dioxide, 2-amino-5-methyl-thiazole and p-toluenesulfonic acid analogous to Example 15 with a yield of 48% of theory.

M.p.: 254° C. (from ethylene chloride).
$C_{14}H_{13}N_3O_4S_2$ (351.40)

Calc. C-47.85%; H-3.73%; N-11.96%; S-18.21%.
Found: C-47.80%; H-3.79%; N-12.00%; S-18.05%.

EXAMPLE 17

2-Ethyl-4-hydroxy-N-(5-methyl-2-thiazolyl)-2H-1,2-benzothiazine-3-carboxamide-1,1-dioxide 0.94 gm (6 millimols) of ethyl iodide were added to a solution of 0.7 gm (2 millimols) of 4-hydroxy-N-(5-methyl-2-thiazolyl)-2H-1,2-benzothiazine-3-carboxamide-1,1-dioxide in 30 ml of methanol and 2.0 ml of 1N sodium hydroxide. The reaction mixture was stirred for 24 hours at room temperature, then neutralized and evaporated in vacuo. The residue was purified by column chromatography (Merck-silica gel 60, particle size:

0.2–0.5 mm; eluant: chloroform/ethanol 95:5), yielding 0.35 mgm (48% of theory) of 2-ethyl-4-hydroxy-N-(5-methyl-2-thiazolyl)-2H-1,2-benzothiazine-3-carboxamide-1,1-dioxide after recrystallization from xylene.

M.p.: 247° C. (decomp.) from xylene.

When sodium hydroxide was replaced by potassium hydroxide, sodium methylate or potassium tert. butylate similar yields were obtained.

$C_{15}H_{15}N_3O_4S_2$ (365.43)
Calc.: C-49.30%; H-4.14%; N-11.50%; S-17.55%.
Found: C-49.20%; H-4.24%; N-11.60%; S-17.42%.

EXAMPLE 18

4-Hydroxy-2-methyl-N-(5-methyl-2-thiazolyl)-2H-1,2-benzothiazine-3-carboxamide-1,1-dioxide Prepared from 4-hydroxy-N-(5-methyl-2-thiazolyl)-2H-1,2-benzothiazine-3-carboxamide-1,1-dioxide and methyl iodide analogous to Example 17 with a yield of 40% of theory. When ethanol was used as the solvent, the yield was 30%.

M.p.: 254° C. (decomp.) from ethylene chloride.
$C_{14}H_{13}N_3O_4S_2$ (351.40)
Calc.: C-47.85%; H-3.73%; N-11.96%; S-18.21%.
Found: C-48.00%; H-3.69%; N-12.02%; S-18.01%.

When methyl bromide was used the same product was obtained after refluxing the methanolic solution for 6 hours.

The reaction was also carried out in n-propanol, dimethylformamide, dimethylacetamide and hexamethylphosphoric acid triamide at temperatures between 40° to 60° C. The yields were 20% of theory.

EXAMPLE 19

4-Hydroxy-2-methyl-N-(5-methyl-2-thiazolyl)-2H-1,2-benzothiazine-3-carboxamide-1,1-dioxide 0.5 ml of 48% hydrobromic acid and 1 ml of glacial acetic acid were added to 0.2 gm (0.55 millimols) of 4-methoxy-2-methyl-N-(5-methyl-2-thiazolyl)-2H-1,2-benzothiazine-3-cabroxamide-1,1-dioxide. After standing for 24 hours, the reaction mixture was heated for two hours on a water bath and was subsequently evaporated in vacuo to dryness. The residue was dissolved in methylene chloride, and the solution was washed with water. After drying and evaporating of the organic phase, 4-hydroxy-2-methyl-N-(5-methyl-2-thiazolyl)-2H-1,2-benzothiazine-3-carboxamide-1,1-dioxide was obtained with a yield of 0.1 gm (52% of theory).

M.p.: 254° C. (decomp.) from ethylene chloride.
$C_{14}H_{13}N_3O_4S_2$ (351.40)
Calc.: C-47.85%; H-3.73%; N-11.96% S-18.21%.
Found: C-47.82%; H-3.67%; N-11.80% S-18.01%

The starting compound was prepared as follows:

26.9 gm (0.1 mol) of methyl 4-hydroxy-2-methyl-2H-1,2-benzothiazine-3-carboxylate-1,1-dioxide, 85.1 gm (0.616 mol) of potassium carbonate and 71 gm (0.5 mol) of methyl iodide were refluxed in 1000 ml of acetone for 16 hours. After each 4 hours 14 gm (0.1 mol) of methyl iodide were added to the boiling reaction mixture. Subsequently, the mixture was stirred for 12 hours at room temperature. The precipitate which had formed was filtered off and washed with acetone. The filtrates were evaporated in vacuo, and after recrystallization from carbon tetrachloride 23.5 gm (83% of theory) of methyl 4-methoxy-2-methyl-2H-1,2-benzothiazine-3-carboxylate-1,1-dioxide were obtained.

M.p.: 78° C.

7.8 gm (28 millimols) of methyl 4-methoxy-2-methyl-2H-1,2-benzothiazine-3-carboxylate-1,1-dioxide were dissolved in 75 ml of ethanol and 42 ml of 1N potassium hydroxide were added to the solution. The reaction mixture was refluxed for 6 hours, stirred overnight at room temperature, and subsequently evaporated in vacuo. The residue was dissolved in water and extracted with ether. The aqueous phase was acidified while cooling, and the precipitate was filtered off and washed with water:

Yield: 6.3 gm (84% of theory) of 4-methoxy-2-methyl-2H-1,2-benzothiazine-3-carboxylic acid-1,1-dioxide.
M.p.: 220° C.

6.2 gm (23 millimols) of 4-methoxy-2-methyl-2H-1,2-benzothiazine-3-carboxylic acid-1,1-dioxide were suspended in 60 ml of benzene and 8.2 ml (0.11 millimols) of thionyl chloride and 0.5 ml of anhydrous dimethylformamide were added to the suspension. The reaction mixture was refluxed for 6 hours, stirred overnight at room temperature and evaporated in vacuo. The residue was dissolved in a little toluene, and the solution was evaporated, yielding 6.9 gm (100% of theory) of 4-methoxy-2-methyl-2H-1,2-benzothiazine-3-carboxylic acid chloride-1,1-dioxide.

M.p.: 117° C.

A solution of 4.7 gm (16 millimols) of 4-methoxy-2-methyl-2H-1,2-benzothiazine-3-carboxylic acid chloride-1,1-dioxide in 150 ml of dry benzene was added dropwise to a solution of 1.8 gm (16 millimols) of 2-amino-5-methylthiazole and 1.6 gm (16 millimols) of triethylamine in 100 ml of dry benzene over a period of 1.5 hours at a temperature of 20° to 30° C. Subsequently the mixture was stirred for 2 hours at room temperature and then refluxed for 1 hour. The reaction mixture was filtered while hot, and petroleum ether was added to the filtrate. Upon cooling, 3.1 gm of 2,5-dimethyl-5H,6H-thiazolo[2',3'-2,3]-pyrimido[5,4-c]-1,2-benzothiazine-5-one-7,7-dioxide crystallized out.

M.p.: 305° C. (decomp.) from ethyl acetate.

From the mother liquor 1.8 gm (31% of theory) of 4-methoxy-2-methyl-N-(5-methyl-2-thiazolyl)-2H-1,2-benzothiazine-3-carboxamide-1,1-dioxide were obtained by evaporating to dryness and recrystallization of the residue from ethyl acetate.

M.p.: 201° C.

$C_{15}H_{15}N_3O_4S_2$ (365.44)
Calc.: C-49.30%; H-4.14%; N-11.50%; S-17.55%.
Found: C-49.45%; H-4.07%; N-11.43%; S-17.70%.

The compounds of this invention, that is, those embraced by formula I above and their non-toxic, pharmacologically acceptable salts formed with inorganic or organic bases, have useful pharmacodynamic properties. More particularly, they exhibit strong anti-inflammatory and antithrombotic activities and reduce the pain due to inflammation in warm-blooded animals such as rats, and are therefore useful for the treatment of rheumatic disorders.

The above-indicated properties of the compounds of the present invention and their acute toxicities were ascertained by the pharmacological test methods described below and compared with those of two known, closely related compounds. The tables show the results of these tests for a representative species of the genus represented by formula I, as well as for the two prior art compounds, where A = 4-Hydroxy-2-methyl-N-(5-methyl-2-thiazolyl)-2H-1,2-benzothiazine-3-carboxamide-1,1-dioxide (invention), B=4-Hydroxy-2-methyl-N-(4-methyl-2-thiazolyl)-2H-1,2-benzothiazine-3-carboxamide-1,1-dioxide (prior art), and C=4-Hydroxy-2-methyl-N-(2thiazolyl)-2H-1,2-benzothiazine-3-carboxamide-1,1-dioxide (prior art).

Determination of activity against adjuvant arthritis in the rat 0.1 ml of a 1% suspension of M. butyricum in viscous paraffin oil was administered by subplantar injection to the right hind paw of male Chbb:THOM-rats having an average body weight of 210 gm at the beginning of the test. The test compounds were administered perorally once a day, starting with the day of the M. butyricum injection, as a trituration in 1% methyl cellulose (1 ml/100 gm animal) for a period of 20 days by means of an esophageal sound.

On the 21st day after induction of the arthritis, the volumes of the right hind paws (unspecific primary reaction at the place of injection) and of the left hind paws (immunologically caused specific secondary reactions) of the animals treated with the test compounds were compared with those of control animals treated by a dummy procedure. Using a linear regression analysis, an $ED_{50}$ with the confidence limits according to FIELLER [Quart. J. Pharm. Pharmacol. 17, 117 (1944)] was calculated as the dosage which reduces the swelling of the paws by 50% in comparison to the control animals.

Determination of the ulcerogenic effect on the stomach of the rat

The test was carried out on male Chbb:THOM-rats with an average body weight of 130 gm at the beginning of the study. The animals were fed with a standard diet (Altromin-R) ad libitum. The test compounds were administered perorally as a trituration in 1% methyl cellulose (1 ml/100 gm animal) by means of an esophageal sound once a day on three successive days. Four hours after the last administration the animals were killed. The stomachs were dissected and the mucosa was washed with water for subsequent macroscopic evaluation. From the percentage of the animals which showed at least one stomach ulcer or one hemorrhagic erosion, the $ED_{50}$ was calculated, using the method of LITCHFIELD and WILCOXON [J. Pharmacol. exp. Therap. 96, 99 (1949)].

Determination of the acute toxicity

The acute toxicity was determined on male and female Chbb: NMRI (SPF)-mice (sex ratio of each dosage group 1:1) having an average body weight of 20 gm. The test compound was administered perorally as a trituration in 1% of methyl cellulose (0.2 ml/10 gm animal) by means of an esophageal sound.

The calculation of the $LD_{50}$-values was effected according to the method of LITCHFIELD and WILCOXON, based on the percentage of animals which died within 14 days after administration of each dose.

Results

The results obtained from these tests are shown in the tables I to III.

Compound A shows, with regard to its effect on the inflammatory primary reactions of the rat at the place of the injection of the adjuvant, an activity which is three times greater than that of compound C. With regard to its efect on the immunologically caused specific secondary reactions at the contralateral paw (specific secondary reaction), compound A is about 5 times more effective than compound C. Surprisingly, the stomach compatibility of compound A is significantly better than that of compound C. Despite the weaker antiphlogistic activity, compound C exerts a two times stronger ulcerogenic effect on the stomach of the rats than compound A. The therapeutic ratio of compound A is about 7 times greater than that of compound C (see table IV).

Compound B does not completely reach the antiphlogistic activity of compound A. The decisive disadvantage of compound B is its strong ulcerogenic effect on the stomach (more than 6 times stronger than that of compound A).

Since the ulcerogenic activity of compound B is relatively more pronounced than its antiphlogistic activity, compound B cannot be therapeutically used as an antiphlogistic. The therapeutic ratio of compound B is still smaller than that of compound C (see table IV). The therapeutic ratio of compound A is 10 times greater than that of compound B. As to the acute toxicity, no significant difference could be observed between the 3 compounds. This means that the difference between the antiphlogistically active doses and the toxic doses in compound A is distinctly higher than in the other compounds (see table V). However, this result is of minor importance. If non-steroidal antiphlogistics are therapeutically used, the acute toxicity does not show a dose-limiting effect. In this group of pharmaceuticals it is instead the ulcerogenic activity in the gastro-intestinal tract which limits the daily dose over long periods of administration.

TABLE I

Comparison of the activity against adjuvant arthritis in the rat after daily oral administration of a period of 21 days on the basis of the $ED_{50}$

| Compound | Activity against the primary reaction $ED_{50}$ mgm/kg (+) | Activity against the secondary reaction $ED_{50}$ mgm/kg (+) |
| --- | --- | --- |
| A | 0.28 (0.14–0.61) | 0.12 (0.09–0.14) |
| B | 0.37 (0.30–0.48) | 0.21 (0.15–0.28) |
| C | 0.77 (0.60–0.88) | 0.60 (0.45–0.83) |

(+) dose per day

TABLE II

Ulcerogenic activity in the stomach of the rat after daily oral administration for a period of 3 days.

| Compound | $ED_{50}$ mgm/kg |
| --- | --- |
| A | 2.31 (1.57–3.41) |
| B | 0.31 (0.21–0.46) |
| C | 0.95 (0.53–1.69) |

TABLE III

Acute toxicity in the mouse after oral administration.

| Compound | $LD_{50}$ mgm/kg |
| --- | --- |
| A | 470 (394–562) |
| B | 488 (287–830) |
| C | 466 (398–545) |

TABLE IV

| | Comparison of therapeutic ratio. | | |
| --- | --- | --- | --- |
| | I | II ED$_{50}$ adjuvant arthritis | |
| Compound | ED$_{50}$ ulcer mgm/kg | prim. reaction mgm/kg | Therapeutic Ratio I/II |
| A | 2.31 | 0.28 | 8.25 |
| B | 0.31 | 0.37 | 0.84 |
| C | 0.95 | 0.77 | 1.23 |

TABLE V

| | Comparison of therapeutic ratio. | | |
| --- | --- | --- | --- |
| | I | II ED$_{50}$ adjuvant arthritis prim. reaction | Therapeutic Ratio |
| Compound | LD$_{50}$ mgm/kg | mgm/kg | I/II |
| A | 470 | 0.28 | 1,679 |
| B | 488 | 0.37 | 1,319 |
| C | 466 | 0.77 | 12 605 |

The activity against the pain caused by inflammation was tested according to Randall and Selitto [Arch. Int. Pharmacodyn. 111, 409 (1957] in male Chbb:THOM-rats, having a body weight of 100 to 130 gm. The test compounds were administered perorally 90 minutes after the induction of the yeast edema by means of an esophageal tube. After further 90 minutes the pain threshold was determined in the animals treated with the test compound and in the control animals treated only with the vehicle methyl cellulose, and by using a linear regression analysis an ED$_{50}$ was calculated with the confidence limits according to FIELLER, the ED$_{50}$ being the dose which increased the pain threshold by 50%.

The following Table VI shows the results obtained from this test.

In the pharmacological test in the rat Compound A, in comparison with compound C, shows an increased effectiveness against the pain caused by inflammation.

TABLE VI

| Compound | Randall-Selitto ED$_{50}$ mgm/kg |
| --- | --- |
| A | 5.6 |
| C | 9.2 |

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective oral dosage unit of the compounds according to the present invention is from 0.03 to 1.67 mgm/kg body weight, preferably 0.08 to 0.42 mgm/kg body weight. The daily dose rate is from 0.08 to 3.33 mgm/kg, preferably 0.16 to 0.83 mgm/kg.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 20

Tablets

The tablet composition is compounded from the following ingredients:

| | |
| --- | --- |
| 4-Hydroxy-2-methyl-N-(5-methyl-2-thiazolyl)-2H-1,2-benzothiazine-3-carboxamide-1,1-dioxide | 10.0 parts |
| Corn starch | 112.0 parts |
| Polyvinylpyrrolidone | 175.0 parts |
| Magnesium stearate | 3.0 parts |
| Total | 300.0 parts |

Preparation:

The active ingredient and the corn starch are intimately admixed with each other, the mixture is moistened with an aqueous 14% solution of the polyvinylpyrrolidone, and the moist mass is granulated through a 1.5 mm-mesh screen. The moist granulate is dried at 45° C. and again passed through the screen, admixed with the magnesium stearate, and the mixture is compressed into 300 mgm-tablets. Each tablet is an oral dosage unit composition containing 10 mgm of the active ingredient.

EXAMPLE 21

Coated Pills

The pill core composition is compounded from the following ingredients:

| | |
| --- | --- |
| 4-Hydroxy-2-methyl-N-(5-methyl-2-thiazolyl)-2H-1,2-benzothiazine-3-carboxamide-1,1-dioxide | 10.0 parts |
| Corn starch | 260.0 parts |
| Gelatin | 8.0 parts |
| Talcum | 18.0 parts |
| Magnesium stearate | 4.0 parts |
| Total | 300.0 parts |

Preparation:

The active ingredient and the corn starch are intimately admixed with each other, the mixture is moistened with an aqueous 10% solution of the gelatin and the moist mass is granulated through a 1.5 mm-mesh screen. The moist granulate is dried at 45° C., again passed through the screen, admixed with the talcum and the magnesium stearate, and the composition is compressed into 300 mgm-pill cores which are subsequently coated with a thin shell consisting essentially of a mixture of talcum and sugar, and finally polished with beeswax. Each coated pill is an oral dosage unit composition containing 10 mgm of the active ingredient.

EXAMPLE 22

Gelatin capsules

The capsule filler composition is compounded from the following ingredients:

| | |
| --- | --- |
| 4-Hydroxy-2-methyl-N-(5-methyl-2-thiazolyl)-2H-1,2-benzothiazine-3-carboxamide-1,1-dioxide | 5.0 parts |
| Corn starch | 385.0 parts |
| Colloidal silicic acid | 6.0 parts |
| Magnesium stearate | 4.0 parts |

-continued

| | Total 400.0 parts |
|---|---|

Preparation:

The ingredients are intimately admixed with each other by milling, and 400 mgm-portions of the mixture are filled into No. 1 gelatin capsules. Each capsule is an oral dosage unit composition containing 5 mgm of the active ingredient.

EXAMPLE 23

Suppositories

The suppository composition is compounded from the following ingredients:

| 4-Hydroxy-2-methyl-N-(5-methyl-2-thiazolyl)-2H-1,2-benzothiazine-3-carboxamide-1,1-dioxide | 25.0 parts |
|---|---|
| Suppository base (e.g. cocoa butter) | 1725.0 parts |
| Total | 1750.0 parts |

Preparation:

The finely pulverized active ingredient is homogeneously blended with the aid of an immersion homogenizer into the suppository base which had been melted and cooled to 40° C. The composition is cooled to 38° C., and 1.75 gm-portions thereof are poured into cooled suppository molds and allowed to harden therein. Each suppository is a rectal dosage unit composition containing 25 mgm of the active ingredient.

EXAMPLE 24

Suspension

The suspension is compounded from the following ingredients:

| 4-Hydroxy-2-methyl-N-(5-methyl-2-thiazolyl)-2H-1,2-benzothiazine-3-carboxamide-1,1-dioxide | 0.5 | parts |
|---|---|---|
| Dioctyl sodium sulfosuccinate (DOSSS) | 0.02 | parts |
| Benzoic acid | 0.1 | parts |
| Sodium cyclamate | 0.2 | parts |
| Colloidal silicic acid | 1.0 | parts |
| Polyvinylpyrrolidone | 0.1 | parts |
| Glycerin | 25.0 | parts |
| Flavoring | 0.1 | parts |
| Distilled water g.s. ad | 100.0 | parts by vol. |

Preparation:

The DOSSS, the benzoic acid, the sodium cyclamate, and the polyvinylpyrrolidone are successively dissolved in a sufficient amount of distilled water at 70° C., the glycerin and the colloidal silicic acid are added to the solution, and the mixture is cooled to room temperature. The finely pulverized active ingredient is suspended in the cooled mixture with the aid of an immersion homogenizer, the flavoring is added, and the suspension is diluted with distilled water to the indicated volume. 5 ml of the suspension are an oral dosage unit composition containing 25 mgm of the active ingredient.

EXAMPLE 25

Injectable solution

The solution is compounded from the following ingredients:

| N-Methyl-D-glucamine salt of 4-hydroxy-2-methyl-N-(5-methyl-2-thiazolyl)-2H-1,2-benzothiazine-3-carboxamide-1,1-dioxide | 20 parts |
|---|---|
| Sodium chloride | 80 parts |
| Distilled, pyrogen-free water g.s. ad | 10,000 parts by vol. |

Preparation:

The active ingredient is dissolved in a sufficient amount of distilled water, the sodium chloride is added to the solution to make it isotonic, and the solution is diluted to the indicated volume with additional distilled, pyrogen-free water. The finished solution is filtered through a membrane filter (0.2 μm), and the filtrate is filled under sterile conditions into sterilized 10 ml-ampules which are then sealed. The contents of each ampule are an injectable dosage unit composition containing 20 mgm of the active ingredient.

Any one of the other compounds embraced by formula I or a non-toxic, pharmacologically acceptable salt thereof may be substituted for the particular active ingredient in Examples 20 through 25. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

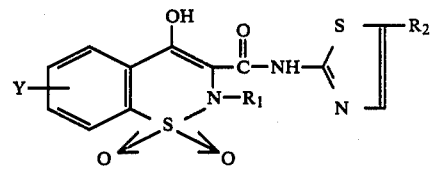

wherein
$R_1$ is hydrogen, methyl or ethyl;
$R_2$ is methyl, ethyl or n-propyl; and
Y is hydrogen, methyl, methoxy, fluorine or chlorine or a non-toxic, pharmacologically acceptable salt thereof formed with an inorganic or organic base.

2. A compound of claim 1, which is 4-hydroxy-2-methyl-N-(5-methyl-2-thiazolyl)-2H-1,2-benzothiazine-3-carboxamide-1,1-dioxide or a non-toxic, pharmacologically acceptable salt thereof formed with an inorganic or organic base.

3. A compound of claim 1, which is the N-methyl-D-glucamine salt of a 4-hydroxy-2H-1,2-benzothiazine-3-carboxamide-1,1-dioxide of claim 1.

4. An antiphlogistic pharmaceutical dosage unit composition consisting essentially of an inert pharmaceutical carrier and an effective antiphlogistic amount of a compound of claim 1.

5. The method of counteracting inflammation and fever in a warm-blooded animal in need thereof, which comprises perorally, parenterally or rectally administering to said animal an effective antiphlogistic amount of a compound of claim 1.

* * * * *

UNITED STATES PATENT AND TRADEMARK OFFICE
CERTIFICATE OF CORRECTION

PATENT NO. : 4,233,299

DATED : November 11, 1980

INVENTOR(S) : GÜNTER TRUMMLITZ ET AL.

It is certified that error appears in the above—identified patent and that said Letters Patent is hereby corrected as shown below:

Column 4, line 53: "3.36 (d, 3," should read -- 2.36 (d, 3, --.

line 54: "$C_{14}H_{13}N_{31}O_4S_2$" should read

-- $C_{14}H_{13}N_3O_4S_2$ --.

Column 6, line 5: "4-Hydroxy-2-methyl-N-(5-N-(5-n- ..."

should read

-- 4-Hydroxy-2-methyl-N-(5-n-  ...  --.

line 9: "5n-propyl" should read -- 5-n-propyl --.

line 29: "3carboxamide" should read

-- 3-carboxamide --.

Column 7, line 7: "3-caboxylate" should read -- 3-carboxylate-- line 64: "caboxamide" should read -- carboxamide --.

Column 13, line 4: "(2thiazolyl)" should read

-- (2-thiazolyl) --

UNITED STATES PATENT AND TRADEMARK OFFICE
CERTIFICATE OF CORRECTION

PATENT NO. : 4,233,299
DATED : November 11, 1980
INVENTOR(S) : GÜNTER TRUMMLITZ ET AL.

It is certified that error appears in the above—identified patent and that said Letters Patent is hereby corrected as shown below:

Column 15, Table V: The therapeutic ratio of compound C should be corrected from "12 605" to -- 605 --.

Signed and Sealed this

Thirteenth Day of January 1981

[SEAL]

Attest:

SIDNEY A. DIAMOND

Attesting Officer

Commissioner of Patents and Trademarks